United States Patent [19]

Beck et al.

[11] 4,251,669
[45] Feb. 17, 1981

[54] ANALOGUES OF PROSTANOIC ACIDS

[75] Inventors: Gerhard Beck, Frankfurt am Main; Wilhelm Bartmann, Bad Soden; Ulrich Lerch, Hofheim; Bernward Schökens, Kelkheim, all of Fed. Rep. of Germany

[73] Assignee: Hoechst Aktiengesellschaft, Frankfurt am Main, Fed. Rep. of Germany

[21] Appl. No.: 870,658

[22] Filed: Jan. 19, 1978

Related U.S. Application Data

[63] Continuation-in-part of Ser. No. 597,667, Jul. 21, 1975, abandoned.

[30] Foreign Application Priority Data

Jul. 23, 1974 [DE] Fed. Rep. of Germany ....... 2435331

[51] Int. Cl.³ .......................................... C07C 177/00
[52] U.S. Cl. .................................... 560/121; 424/305; 424/317; 562/433; 562/463; 562/465; 562/472; 562/503; 260/343.3 P; 260/345.7 P; 260/345.8 P
[58] Field of Search ................ 560/121; 562/463, 465, 562/472; 424/302, 317

[56] References Cited

PUBLICATIONS

Derwent Abstract 79627X/43 12T2610-718 31.03.75.
Derwent Abstract 38270V/21 BE 807.047 08.11.72.

Primary Examiner—Paul J. Killos
Attorney, Agent, or Firm—Curtis, Morris & Safford

[57] ABSTRACT

The present invention relates to new analogues which do not occur naturally of prostanoic acids of the formula I

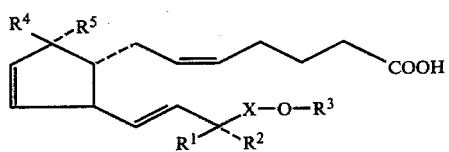

The compounds of the invention have spasmogenic, bronchodilatant and hypotensive properties. Therefore, they can be used as medicaments.

This invention also relates to a process for preparing the compounds of the invention.

10 Claims, No Drawings

ANALOGUES OF PROSTANOIC ACIDS

The present invention relates to analogues of prostanoic acids and to a process for their manufacture.

Prostaglandins are a group of natural substances which have been isolated from various animal tissues. They are responsible for a large number of physiological effects in mammals. The natural prostaglandins have a carbon skeleton of generally 20 carbon atoms and differ chiefly in a major or minor content of hydroxyl groups or double bonds in the cyclopentane ring (the structure and action of prostaglandins are described, inter alia, in M.F. Cuthbert "The Prostaglandins, Pharmacological and Therapeutic advances", William Heinemann Medical Books, Ltd., London 1973).

The synthesis of analogues of prostane acids which do not occur naturally and in which the large number of pharmacological actions of the natural prostane acids are differentiated, acquires an increasing importance.

The present invention relates to new analogues which do not occur naturally, of prostanoic acids of the formula I

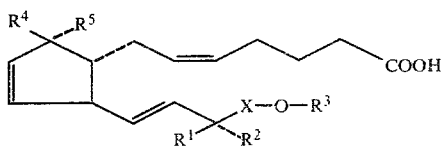

which comprises both the optically active compounds of the natural configuration and the racemic compounds and in which: $R^1$ and $R^2$ each is hydrogen or a hydroxyl group, $R^1$ and $R^2$ being different, $R^3$ is a saturated or unsaturated, straight-chain or branched aliphatic hydrocarbon radical having 1–8 carbon atoms, a straight-chain or branched oxo-alkyl radical having 2–8 carbon atoms and the oximes, oxime ethers, ethylene glycol acetals and ethylene thioglycol acetals, a straight-chain or branched hydroxyalkyl radical having 2–8 carbon atoms, the OH-group being in end position, or a straight-chain or branched carboxylalkyl radical of 2–8 carbon atoms, $R^4$ and $R^5$ conjointly denote oxygen or each is hydrogen or a hydroxyl group, $R^4$ and $R^5$ being different, X is a saturated, branched alkylene group having 2–5 carbon atoms, or an aryl or benzyl radical which may be substituted by one or several lower alkyl or alkoxy groups, one or several halogen atoms or trifluoromethyl groups, or an $\alpha$- or $\beta$-furfuryl radical, and their physiologically acceptable salts with organic or inorganic bases and their esters with aliphatic, cycloaliphatic or araliphatic alcohols having 1–8 carbon atoms in the ester portion.

The invention further relates to a process for the manufacture of new analogues which do not occur naturally, of prostanoic acids of the formula I, to their physiologically acceptable salts with organic and inorganic bases and to their esters having 1–8 carbon atoms in the ester portion, as well as to pharmaceutical preparations containing these active compounds.

The process is characterized in that
(a) a compound of the formula II

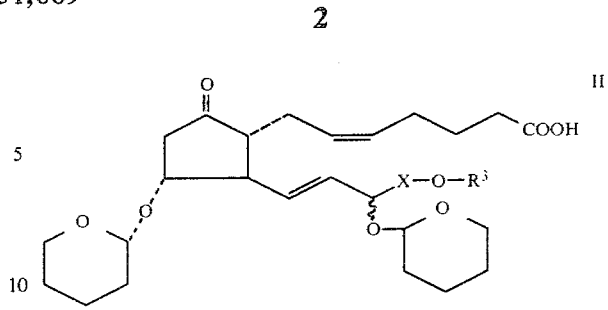

or of the formula III

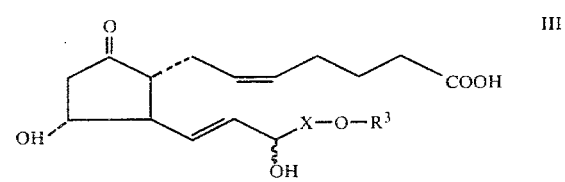

in which X and $R^3$ each is defined as in formula I, are converted into a compound of the formula I in the presence of strong acids and optionally the compound of the formula I in which $R^4$ and $R^5$ conjointly denote an oxygen atom, is reduced as pure epimer or as 15-epimer mixture with a complex metal hydride to a compound of the formula I in which $R^4$ and $R^5$ are not identical and each is hydrogen or a hydroxyl group, or (b$_1$) an alcohol of the formula IV

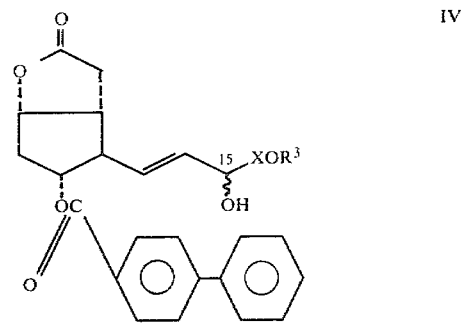

in which $R^3$ is defined as in formula I, is converted as epimer mixture or after separation of the epimers by acid-catalized addition of 2,3-dihydropyran into a tetrahydropyranyl ether of the formula V

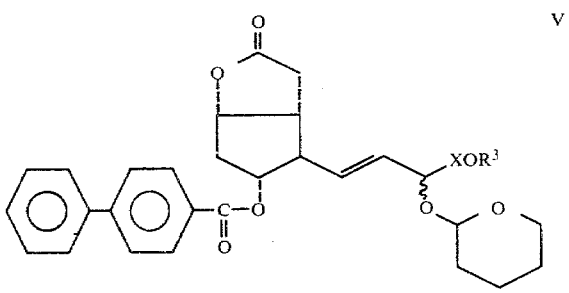

in which X and $R^3$ are defined as in formula I, (b$_2$) the ether of the formula V is converted by basic-catalized ester separation into an alcohol of the formula VI

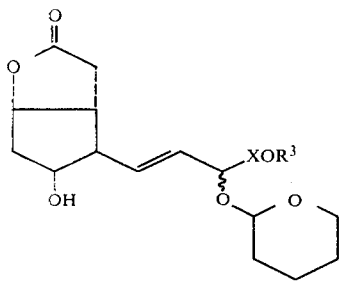

in which X and R³ are defined as in formula I (b₃) an alcohol of the formula VI is reacted with p-toluene-sulfochloride to a sulfonic acid ester of the formula VII

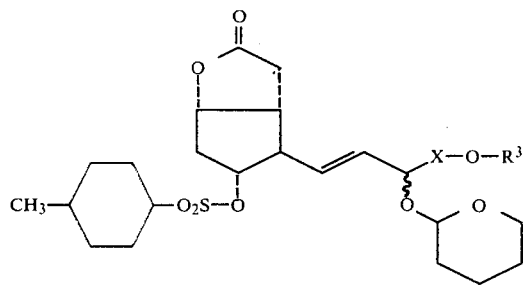

in which X and R³ are defined as in formula I, (b₄) the sulfonic acid ester so obtained of the formula VII is reacted in the presence of bases to an unsaturated lactone of the formula VIII

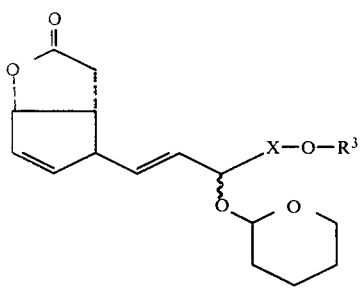

in which X and R³ are defined as in formula I, (b₅) the unsaturated lactone of the formula VIII is converted with a complex aluminum hydride into a lactol of the formula IX

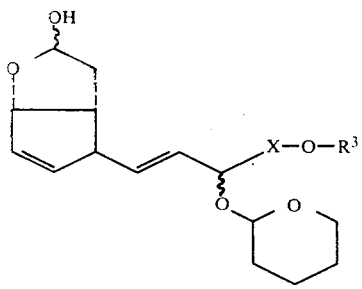

in which X and R³ are defined as in formula I, (b₆) the lactol of the formula IX is reacted with an ylide of 4-carboxybutyl-triphenylphosphonium bromide in a solution of sodium hydride in dimethyl sulfoxide to give an acid of the formula X,

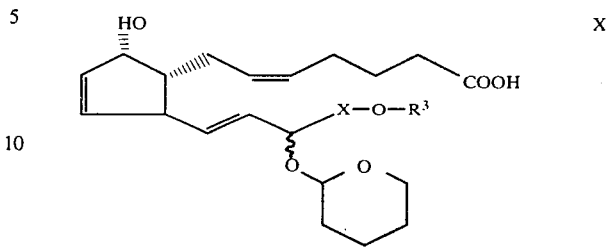

in which X and R³ are defined as in formula I, (b₇) the compound of the formula X is oxidized to a compound of the formula XI

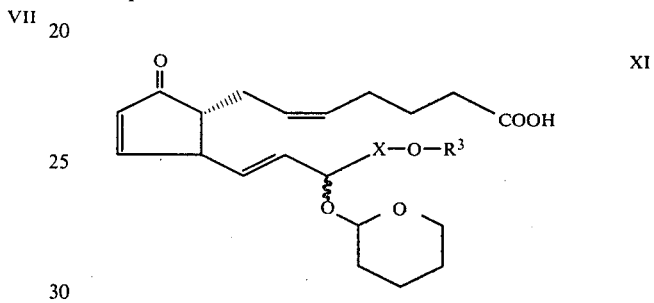

in which X and R³ are defind as in formula I, (b₈) the tetrahydropyranyl ether protective group is eliminated in a compound of formula X or XI by acid hydrolysis, yielding a compound of formula I which is optionally reduced in form of the pure epimers or as 15-epimer mixture with a complex metal hydride to a compound of the formula I, wherein R⁴ and R⁵ are different and each is hydrogen or a hydroxyl group, or (c₁) the alcohol of the formula XII

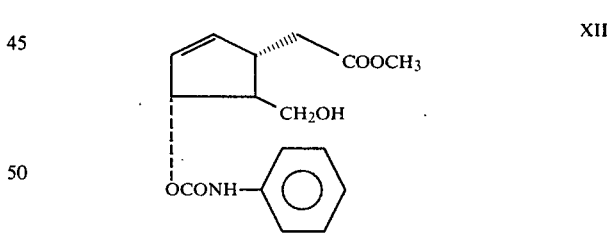

is oxidized to the aldehyde of the formula XIII

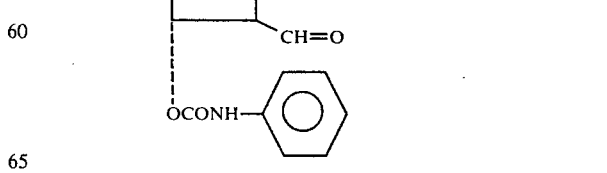

(c₂) the aldehyde of the formula XIII is reacted with a phosphonate of the formula XIV

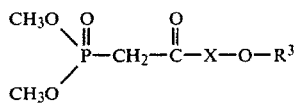  XIV in which X and R³ are defined as in formula I, to a compound of the formula XV

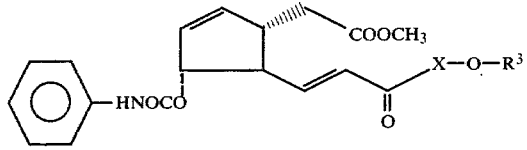  XV (c₃) the compound of the formula XV is reduced with a complex metal hydride to the epimer mixture of the alcohols of the formula XVI

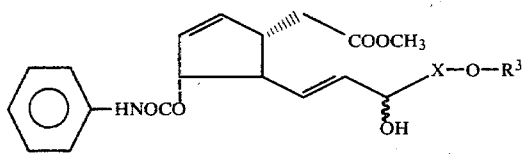  XVI in which X and R³ are defined as in formula I, (c₄) the ester function of the compound of formula XVI is saponified in the presence of dilute aqueous bases to the free acid of the formula XVII

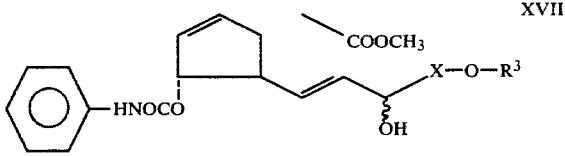  XVII in which X and R³ are defined as in formula I, (c₅) the compound of the formula XVII is converted by heating in organic solvents in the presence of water into an unsaturated hydroxylactone of the formula XVIII

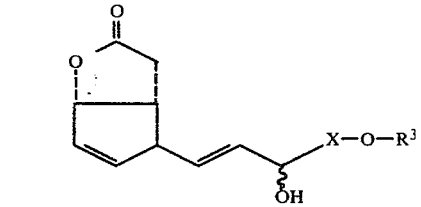  XVIII in which X and R³ are defind as in formula I, (c₆) the unsaturated hydroxylactone of the formula XVIII is converted as epimer mixture or after separation of the epimers by acid-catalized addition of 2,3-dihydropyrane into the compound of the formula VIII

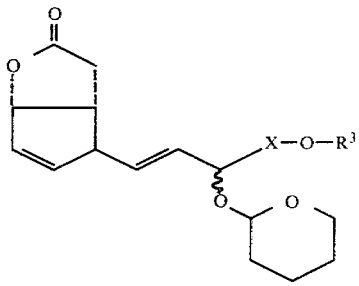  VIII in which X and R³ are defined as in formula I, and the compound of the formula VIII is converted as described under b₅ and b₈ into a compound of the formula I and the compound of the formula I obtained according to (a), (b) or (c) is converted, if desired, into physiologically acceptable salts or esters.

Of the radicals mentioned for the substituent R³, lower alkyl radicals, especially the methyl, ethyl, propyl and isobutyl group are preferred, if R³ denotes a saturated, straight-chain or branched radical, moreover lower alkenyl radicals, especially the allyl radical, if R³ denotes an unsaturated, straight-chain radical. Particularly suitable representatives of the oxo-alkyl radicals mentioned are the straight-chain or branched C₂-C₅ oxoalkyl radicals having a terminal oxo group, and oximes, oxime ethers, ethylene glycols and ethylene thioglycol acetals thereof, preferably the 3-oxopropyl- and 2-dimethyl-3-oxopropyl radical, particularly suitable representatives of the hydroxyalkyl radicals are especially the straight-chain or branched C₂-C₅ hydroxyalkyl radicals, preferably the 3-hydroxypropyl and the 2-dimethyl-3-hydroxypropyl radical, and particularly suitable representatives of the carboxyalkyl radicals are especially the straight-chain or branched C₂-C₅ carboxyalkyl radicals, preferably the 2-carboxyethyl and the 2-dimethyl-2-carboxyethyl radical.

Of the radicals mentioned for X are preferred: the ethylidene group

the isopropylene and isobutylene group, the phenylene and benzylene group which may be substituted by one or several methyl, ethyl, methoxy and/or ethoxy groups, by one or several fluorine and/or chlorine atoms and by one or several trifluoromethyl groups. Especially preferred are the isobutylene, the ethylidene, the 3-chlorophenylene and the 2-methoxybenzylene group.

The process for the manufacture of a compound of formula I starts according to a₁ by the hydrolysis of a compound of formula II to give a compound of formula III.

The compounds of the formula II and III can be prepared as follows:

The primary bicyclic alcohol of the formula XIX

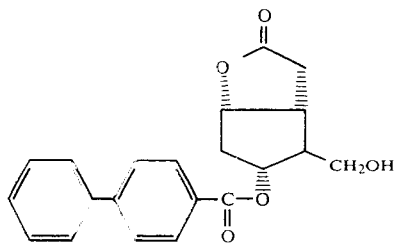

which can be prepared according to E. J. Corey (J. A. Chem. Soc. 93, (1971) pages 1491–1493), is oxidized, for example with the complex compound from thioanisole and chlorine in benzene at −30° C. to −5° C. in an inert atmosphere to the aldehyde of the formula XX

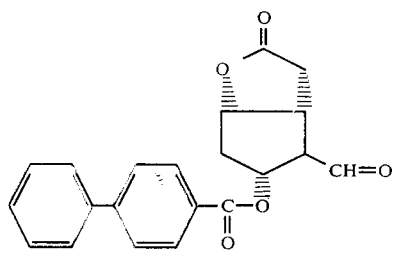

and then, the aldehyde of the formula XX so obtained is reacted according to Horner, Witting, Emmons, with a phosphonate of the formula XXI

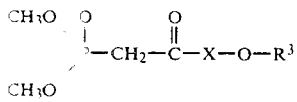

in which X and $R^3$ are defined as in the formula I, to an unsaturated ketone of the formula XXII

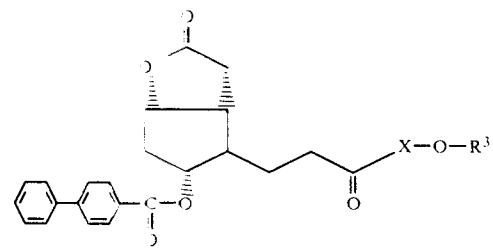

The phosphonic acid ester of the formula XXI can be prepared by reacting an ester of the formula $R^3$-OX-$CO_2$-alkyl with butyl-lithium and methylphosphonic acid dimethyl ester (for example according to Corey, J. Am. Chem. Soc. 88, (1966), 5654). The ketone obtained is then reduced with zinc boronate in etheric solution at 0° C. to room temperature to the epimer mixture of the alcohols of the formula XXIII

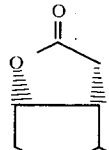
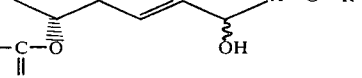

the alcohol obtained of the formula XXIII is converted as epimer mixture or after the separation of the epimers as pure S- or R-epimer with anhydrous potassium carbonate in absolute methanol at room temperature to a diol of the formula XXIV

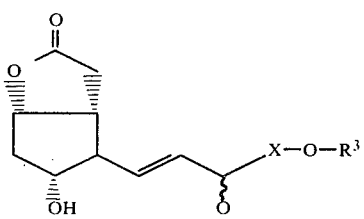

the diol so obtained of the formula XXIV is converted by the addition of 2,3-dihydropyrane in the presence of p-toluenesulfonic acid into a di-tetrahydropyranylether of the formula XXV

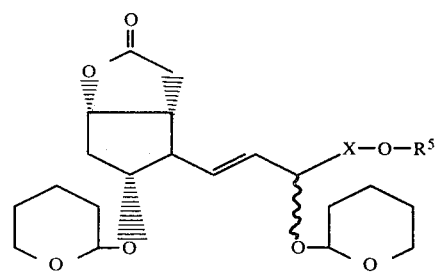

the tetrahydropyranyl ether so obtained of the formula XXV is reduced with diisobutylaluminium hydride in toluene at −60° C. to −70° C. to a lactol of the formula XXVI

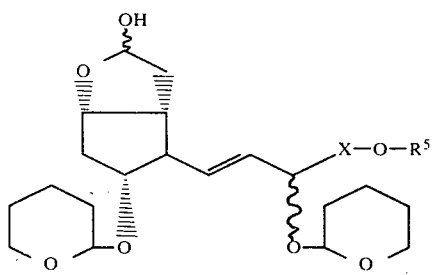

the lactol so obtained of the formula XXVI is reacted with the ylide from 4-carboxybutyltriphenylphosphonium bromide in a solution of sodium hydride in dimethyl sulfoxide according to Wittig (J. Org. Chem. 28, (1963), 1128) to an acid of the formula XXVII

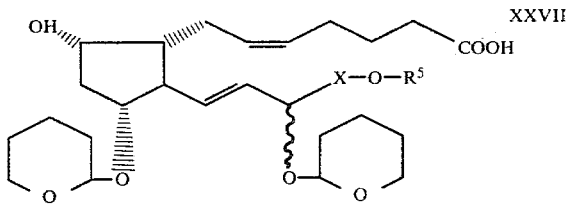

and, finally, the acid so obtained is oxidized at a temperature of about −20° C. with a Jones' reactant (solution of chromium (VI)-oxide in sulfuric acid) in acetone to a compound of the formula II and that compound is optionally converted, while splitting off the ether protective groups by a treatment with a 2% aqueous-alcoholic oxalic acid solution at 20° C. to 50° C. into the compound of the formula III.

The compound of the formula II or III is then converted into a compound of the formula I by means of a strong acid, for example aqueous hydrochloric acid at pH 0.9 to 2.0 at a temperature of from 0° C. to +50° C., preferably +25° to +35° C.

Moreover, compounds of formula I are obtained in which $R^4$ and $R^5$ each is hydrogen or a hydroxyl group, $R^4$ and $R^5$ being different, by reducing a compound of formula I, in which $R^4$ and $R^5$ conjointly denote oxygen, with a complex metal hydride, preferably sodium or zinc boron hydride in an aprotic solvent, such as, for example ether or benzene at a temperature within the range of from −20° C. to +30° C., preferably 0° C. to +20° C.

According to method (b) of the process of the invention, an alcohol of formula IV (corresponding to the formula XXIII in the above reaction scheme) is converted into the tetrahydropyranyl ether of formula V as epimer mixture or in the form of the pure epimer by meams of 2,3-dihydropyran in the presence of acid catalysts, such as, for example, p-toluenesulfonic acid in an aprotic solvent, such as for example methylene chloride or chloroform at room temperature and by splitting off the p-diphenyl ester protective group by organic or inorganic bases, such as, for example potassium carbonate, in the presence of anhydrous alcohols in excess at a temperature within the range of from 0° to 40° C., preferably at room temperature, the compound of formula V is converted into a compound of formula VI.

In general, it is advantageous to purify the tetrahydropyranyl ether of formula V obtained previously by chromatography.

In a further step, the alcohol of formula VI is converted into a sulfonic acid ester of formula VII for which purpose preferably sulfonic chlorides, such as for example p-toluene sulfochloride in the presence of pyridine or piperidine in aprotic solvents, such as methylene chloride or chloroform are used preferably at temperatures within the range of from 0° to +50° C. The sulfonic acid ester of formula VII is then reacted in the presence of bases, preferably with 1,5-diazabicyclo[4,3,0]non-5-ene (cf. H. Oediger et al. Synthesis, 591 (1972)) to give an unsaturated compound of formula VIII.

The unsaturated tetrahydropyranyl ether of formula VIII is reacted in known manner with 1 to 1.5 mols of a complex metal hydride, preferably diisobutyl aluminum hydride in an absolutely anhydrous hydrocarbon, such as for example toluene or xylene at a temperature within the range of from −95° C. to −10° C., preferably from −70° C. to −50° C. to give a lactol ether of formula IX.

The lactol ether so prepared of the formula IX can be reacted without further purification to a carboxylic acid of formula X, the preferred mode of operation of the Wittig reaction being carried out according to J. Org. Chem. 28, 1128 (1963).

By subsequently oxidizing the compound of formula X with chromic acid in aqueous, sulfuric acetone solution (according to Jones) at a temperature below 0° C., preferably at −25° C. to −5° C., a compound of formula XI is obtained.

The ether protective group in the compound of formula X or XI is split off by mild acid hydrolysis, preferably in a 2% aqueous-alcoholic oxalic acid solution at 20° to 50° C., or by heating for 1 to 2 hours in 60% to 70% strength acetic acid to 50° C., a compound of formula I being formed.

If a separation of epimers has not been carried out at the stage of the alcohols of the formula IV, a separation of the epimers of the alcohols in 15 or 9 to 15-position can be carried out by means of the compounds of formula I (for the nomenclature of the prostaglandins, cf. N. Andersen, Annals of the New York Academy of Sciences, Volume 180, Prostaglandins, page 14).

According to method (c) of the process of the invention the ester-alcohol of the formula XII (prepared according to E. J. Corey J. Amer. Chem. Soc. 95, 6831 (1973)) is oxidized as racemate or in the form of pure optical antipodes to give the aldehyde of the formula XIII. The oxidation is carried out according to a method usual for the oxidation of primary alcohols to give aldehydes. A preferred embodiment is the oxidation with chromic acid anhydride in the presence of pyridine, if desired with methylene chloride as solvent, as has been described by Collins in Tetrahedron Lett., 3363 (1968). A further preferred embodiment is the oxidation with chlorine in the presence of thioanisole (cf. Corey and Kinn, J. Org. Chem. 38, (1973) 1233).

In a further step, the aldehyde of formula XIII is reacted according to the Horner-Emmons-Wittig method, with a phosphonic acid ester of formula XIV to yield an unsaturated ketone of formula XV, a preferred embodiment of the reaction consisting in that the sodium salt of the phosphonate of formula XVI is prepared by reacting it with sodium hydride in glycol dimethyl ether and then adding the aldehyde of formula XIII for a reaction time of 2 to 6 hours at room temperature. The phosphonates of formula XV are prepared according to methods known in the literature (cf. for example Corey, J. Am. Chem. Soc. 88, (1966).

The alcohol of formula XVI is obtained in the form of the epimer mixture if a ketone of formula XV is reduced with a complex metal hydride, preferably an alkali metal boranate or sodium-bis-(2-methoxy-ethoxy)-aluminium hydride, the reaction being carried out in hydrocarbons, such as benzene or, preferably in ethers, such as dioxane, dimethoxy ethane or diethylene glycol dimethyl ether or an alcohol-water mixture, for example methanol-water, at a temperature within the range of from −10° to +30° C. The alcohols of the formula XVI are especially suitable for an epimer separation, however, the further reaction can also be carried out with the epimer mixture and the epimers be separated at the stage of the end products.

The ester function of a compound of formula XVI is saponified with aqueous bases, for example alkali metal carbonate or hydroxide at 0° C. to 40° C., a free acid of formula XVII being formed. Then, the acid of formula XVII is converted into a lactone of formula XVIII by simply heating to about 40° to 80° C. in a mixture of water and organic solvents, for example isobutyl ether or dimethoxy ethane at neutral pH value. (This conversion has been described by E. J. Corey in J. Amer. Chem. Soc. 95, 6831 (1973)).

The addition of dihydropyrane, which includes the formation of a tetrahydropyranyl ether, is carried out in an etheric or benzenic solution of an alcohol of formula XVIII in the presence of usual acid catalysts, such as, for example p-toluenesulfonic acid or boron trifluordietherate at room temperature. In general, it is advantageous, to purify the tetrahydropyranyl ether so obtained of formula VIII at that stage by chromatography.

In a further step, the compound of formula VIII is reacted to a compound of formula I as described under (b$_5$) to (b$_8$).

The conversion of the free acid of formula I into physiologically acceptable salts or esters is carried out according to known methods.

According to the process of the invention, the following compounds can be prepared in addition to the compounds cited in the preceding examples:

9-Oxo, 15-hydroxy-16,16-dimethyl-18-oxa-5-cis,10,13-trans-20-nor-prostatrienoic acid.

9-Oxo-, 15-hydroxy-16,16-dimethyl-18-oxa-5-cis,10,13-trans-20,20-homo-prostatetraenoic acid.

9-Oxo-, 15-hydroxy-16,16,20,20-tetramethyl-18-oxa-5-cis,10,13-trans-prostatrienoic acid.

9-Oxo-, 15,20-dihydroxy-16,19,19-trimethyl-17-oxa-5-cis,10,13-trans-prostatrienoic acid.

9-Oxo-, 15-hydroxy-15(3'-chloro-4'-isobutyloxy)-phenyl-5-cis,10,13-trans-20-penta-nor-prostatrienoic acid.

9-Oxo-, 15-hydroxy-16(2'-methoxy-4'-ethoxy)-phenyl-5-cis,10,13-trans-20-tetra-nor-prostatrienoic acid.

9-Oxo-, 15-hydroxy-17-methyl-18-oxa-5cis,10,13 trans-20-nor-prostatrienoic acid.

9-Oxo-, 15,20-dihydroxy-16,19,19-trimethyl-17-oxa-5cis,10,13-trans-prostatrienoic acid.

9-Oxo-, 15,20-dihydroxy-16,16,19,19-tetramethyl-17-oxa-5cis,10,13-trans-prostatrienoic acid.

9-Oxo-, 15-hydroxy-16-methyl-18-oxa-5cis,10,13-trans-20-nor-prostatrienoic acid.

9-Oxo-, 15-hydroxy-16,20,20-trimethyl-18-oxa-5cis,10,13-trans-prostatrienoic acid.

9-Oxo-, 15-hydroxy-16-methyl-18-oxa-5cis,10,13-trans-prostat-trienoic acid.

9-Oxo-, 15,20-dihydroxy-16,16-dimethyl-18-oxa-5cis,10,13-trans-prostatrienoic acid.

9-Oxo-, 15-hydroxy-16,16-dimethyl-17-oxa-5cis,10,13-trans-prostatrienoic acid.

9-Oxo-, 15-hydroxy-16,16-dimethyl-17-oxa-5cis,10,13-trans-20-bis-nor-prostatrienoic acid.

9-Oxo-, 15-hydroxy-16,16-dimethyl-17-oxa-5cis,10,13-trans-20-nor-prostatrienoic acid.

9-Oxo-, 15-hydroxy-16,16,20,20-tetramethyl-17-oxa-5cis,10,13-trans-prostatrienoic acid.

9-Oxo-, 15-hydroxy-16,16,19-trimethyl-17-oxa-5cis-10,13-trans-prostatrienoic acid.

9-Oxo-, 15-hydroxy-16-methyl-17-oxa-5cis-10,13-trans-prostatrienoic acid.

9-Oxo-, 15-hydroxy-16,19-dimethyl-17-oxa-5cis,10,13-trans-prostatrienoic acid.

9-Oxo-, 15-hydroxy-16-methyl-17-oxa-5cis-10,13-trans-20-nor-prostatrienoic acid.

9-Oxo-, 15-hydroxy-16-ethyl-17-oxa-5cis,10,13-trans-20-nor-prostatrienoic acid.

9-Oxo-, 15-hydroxy-16-ethyl-17-oxa-19-methyl-5cis-10,13-trans-prostatrienoic acid.

9-Oxo-, 15-hydroxy-16-ethyl-17-oxa-5cis,10,13-trans-prostatrienoic acid.

9-Oxo, 15-hydroxy-15(3'-chloro-4'-propyloxy)phenyl-5cis,10,13-trans-20-penta-nor-prostatrienoic acid.

9-Oxo-, 15-hydroxy-15(4'-propyloxy)phenyl-5cis-10,13-trans-20-penta-nor-prostatrienoic acid.

9-Oxo-, 15-hydroxy-15(3'-trifluoromethyl-4'-ethoxy)-phenyl-5cis,10,13-trans-20-penta-nor-prostatrienoic acid.

The compounds of the invention have good spasmogenic, bronchodilatant and hypotensive properties, and have a considerably greater stability and longer duration of action compared with the natural prostaglandins E, F and A. Therefore, they can be used as medicaments.

The compounds of the invention can be used as the free acids or in the form of their physiologically tolerable salts with inorganic acids, or as esters of aliphatic, cycloaliphatic or araliphatic alcohols. Suitable salts are, for example alkali metal salts, especially sodium and potassium salts, as well as the salts formed by organic bases, such as, for example benzyl ammonium, triethanol ammonium or morpholine salts, as esters preferably esters of lower saturated, straight-chain or branched aliphatic alcohols, such as methyl, ethyl, propyl, isopropyl, butyl or pentyl esters and benzyl esters.

Acids and salts or esters can be used in the form of their aqueous solution or suspension or also as solutions in pharmacologically tolerable organic solvents, for example, mono- or multivalent alcohols and their glycerol esters, in dimethyl-sulfoxide or dimethyl formamide, but also in the presence of pharmacologically tolerable polymer carriers, for example polyvinyl pyrolidone.

Preparations may be infusion or injection solutions as well as tablets and capsules.

The compounds may be administered alone or also together with other pharmacologically suitable active substances, for example, diuretics or antidiabetics. The suitable daily dose is 1 microgramme to 10 mg/kg body weight, the suitable dosage unit is 0.05 mg to 200 mg of the active substance of the formula I of the invention.

The compounds of the formulae V, VI, VII, VIII, IX, X, XI XV, XVI, XVII, XVIII are valuable intermediates for the synthesis of the compounds of the invention of the formula I.

The following Examples illustrate the invention.

EXAMPLE 1a:

Synthesis of 9-oxo-11α, 15-dihydroxy-16,16-dimethyl-18-oxa-5-cis-13-trans-prostadienoic acid [16,16-dimethyl-18-oxa-PGE$_{2\alpha}$]

15 S and 15 R epimers (III)

0.72 g of the compound 9-oxo-11α,15-bis-tetrahydropyranyloxy-16,16-dimethyl-18-oxa-5-cis-13-trans-prostadienoic acid (II) were dissolved in 5 ml of tetrahydrofurane, 15 ml of acetic acid-water were added in the ratio 2:1 and stirred for 4 hours at 40° C. Then, the solvent was eliminated in vacuo by adding benzene several times, at a temperature not exceeding 5° C.

The yield of compound XII a was 0.6 g of pale oil.

After column chromatography on Merck silica gel (70–230 mesh) with chloroform-methanol (22:1) there were obtained in the fractions (individual fraction: 2 ml) 130–170 104 mg of 15 R epimer III a and the fractions 170–280 102 mg of 15 S epimer III b.

Yield: 0.206 g (41.5%).

Thin-layer chromatogram (solvent: ethyl acetate-acetic acid = 97.5:2.5) (Merck silica gel plates).

$R_f = 0.36$, 15 R epimer
$R_f = 0.28$; 15 S epimer

The spectra for the 15 R epimer and 5 S epimer of III a are practically identical within the scope of the customery resolution.

Absorptions in the infrared spectrum (NaCl plates): 3450 (OH band), 2950, 1745 (ketone-carbonyl), 1720 (acid-carbonyl). 1110, 1040, 970.

NMR spectrum (in CDCl$_3$), δ-values: 0.9 singlet 6 H (CH$_3$), 1.18 triplet 3 H (CH$_3$CH$_2$—), 1.4–2.7 multiplet 12 H (—CH$_2$—, >CH—), 3.28 singlet 2 H (—(CH$_3$)$_2$C—CH$_2$O—), 3.46 quartet 2 H (—OCH$_2$CH$_3$), 3.8–4.4 multiplet 2 H (>CH—OH), 5.25–5.75 multiplet 4 H (olefinic H), 5.9–6.4, large singlet 3 H (2×OH, 1×COOH).

By H/D exchange the signal at 5.9–6.4 can be removed.

EXAMPLE 1b

Synthesis of
9-oxo-11α,15-dihydroxy-16,16,20,20-tetramethyl-18-oxa,5 cis, 13-trans-prostadienoic acid (III b)

10.9 g of the compound 9-oxo-11α,15-bis-tetrahydropyranyloxy-16,16,20,20-tetramethyl-18-oxa-5cis,13-trans-prostadienoic acid (II b) were reacted as described in Example 1a. Yield: 4.7 g of pale oil (after column chromatography on silica gel). Thin-layer chromatography (ethyl acetate: glacial acetic acid = 97.5:2.5).

$R_f = 0.47$, 15 R-epimer
$R_f = 0.40$, 15 S-epimer

The NMR-spectra for the 15 R epimer and the 15 S epimer were identical within the scope of the customary resolution.

EXAMPLE 1c

Synthesis of
9-oxo-11α,15-dihydroxy-16,16-dimethyl-18-oxa-5cis-10,13-trans-20-nor-prostadienoic acid 9.7 g of the compound 9-oxo-11α, 15-tetrahydropyranyloxy-16,16-dimethyl-18-oxa-5cis-10,13-trans-20-nor-prostadienoic acid (II c) were reacted as described in Example 1a.

Yield: 4.6 g of pale oil (after column chromatography on silica gel).

Thin-layer chromatography: (ethyl acetate: glacial acetic acid = 97.5:2.5).

$R_f = 0.59$, 15 R epimer
$R_f = 0.49$, 15 S epimer

EXAMPLE 2a:

Synthesis of
9-oxo-15-hydroxy-16,16-dimethyl-18-oxa-5cis-10,13-trans-prostatrienic acid [16,16-dimethyl-18-oxa-PGA$_2$]

15 S and 15 R epimer (I)

20 mg of compound III (Example 1) were dissolved in 8 ml of aqueous hydrochloric acid, pH 1.5, while thoroughly stirring. The solution was heated to 30°–35° C. for one and a half hours, cooled and the reaction mixture was extracted several times with ethyl acetate. The ethyl acetate phase was separated, dried with MgSO$_4$ and concentrated in vacuo.

Yield: 15.9 mg of pale oil (I).

Thin-layer chromatogram (solvent: ethyl acetate-acetic acid = 97.5:2.5) (Merck silica gel).

$R_f = 0.74$

When the isomer mixture of the compound III (Example 1) is used, the isomer separation of the 15 S or 15 R epimer of compound I occurs by column chromatography on silica gel with a mixture of cyclohexane-ethyl acetate-glacial acetic acid in the ratio 40:60:1.

NMR spectrum (in CDCl$_3$) δ-values: 0.9 singlet 6H (CH$_3$), 1.19 triplet 3 H (CH$_3$—CH$_2$—), 1.4–2.7 multiplet 10 H (—CH$_2$—>CH—), 3.3 singlet 2 H (—CH$_3$.)$_2$—C—OH$_2$—O—), 3.45 quartet 2 H (—OCH$_2$—CH$_3$), 3.85–4.1 multiplet 1 H (>CH—OH), 5.25–5.75 multiplet 4 H (olefinic H), 6.05–6.35 split duplet 1 H (—CH=CH—C=O), 6.6–7.2 large signal 2 H (OH and COOH) 7.4–7.65 split dublet 1 H (—CH=CH—C=O).

By H/D exchange the signal at 6.6–7.2 ppm can be removed.

The NMR spectra for the 15 S or the 15 R isomer are practically identical within the scope of the customary resolution (60 MHz-spectrum).

UV-spectrum (in ethanol) $c = 9.6 \cdot 10^{-5}$ Mol/ltr:λmax = 218 mµ, $\Delta \approx 10.000$.

EXAMPLE 2b:

Synthesis of
9-oxo-15-hydroxy-16,16,20,20-tetramethyl-18-oxa-5cis,10,13-trans-prostatrienoic acid 15 S and 15 R epimer (I)

4.2 g of the compound III b (Example 1b) were reacted as described in Example 2a.

Yield: 2.4 g of oil (I).

Thin-layer chromatography (solvent:ethyl acetate:acetic acid = 97.5:2.5 (on Merck silica gel).

$R_f = 0.56$

NMR-spectrum (in CDCl$_3$) δ-values: 0.8–1.0 singlet, dublet 12 H (CH$_3$), 1.4–2.7 multiplet 10 H (—CH$_2$—,->CH—), 3.15 dublet 2 H (—OCH$_2$CH<), 3.3 singlet 2 H (—CH$_2$—O—) 3.8–4.1 multiplet 1 H (CH—OH), 5.3–5.8, multiplet 4 H (olefinic protons), 6.05–6.35, split doublet

1 H (—CH=CH—C=O), 6.8–7.2 large signal, 2 H (OH, COOH) 7.4–7.65, split doublet 1 H (—CH=CH—C=O).

The signal at 6.8–7.2 ppm can be removed by H/D exchange.

EXAMPLE 2c

Synthesis of
9-oxo-15-hydroxy-16,16-dimethyl-8-oxa-5cis-10,13-trans-20-nor-prostatrienoic acid 15 S epimer and 15 R epimer (I)

3.8 g of the compound III c (Example 1c) were reacted as described in Example 2a.

Yield 2.0 g of pale oil (I).

Thin-layer chromatography (solvent: ethyl acetate-acetic acid = 97.5:2.5 (on Merck silica gel).

$R_f = 0.75$

NMR-spectrum (in CDCl$_3$) δvalues: 0.95 singlet 12 H (CH$_3$) 1.4–2.7 multiplet 10 H (—CH$_2$, >CH—) 3.35 singlet 2 H (—CH$_2$—O), 3.4 singlet 3H (—OCH$_3$), 3.9–4.2 multiplet 1 H (CH—OH), 5.3–5.8 multiplet 4 H (olefinic protons), 6.10–6.35 split doublet 1 H, 6.4–6.8 large signal 2 H (OH, COOH), 7.4–7.65 split doublet 1 H.

The signal at 6.4–6.8 ppm can be removed by H/D exchange.

EXAMPLE 3a

Synthesis of 9-oxo-15S-hydroxy-16,16-dimethyl-18oxa-5cis-10,13-trans-prostadienoic acid (16,16-dimethyl-18oxa-PGA$_2$) I 1.1 g of the compound 9-oxo-11α,15S-bis-tetrahydropyranyloxy-16,16-dimethyl-18-oxa-5cis-13-trans-prostadienoic acid (II) were dissolved in 15 ml of tetrahydrofurane, 25 ml of aqueous hydrochloric acid of pH 1.3 were added and the solution was heated to 35° C. for one and a half hours. Then, the solvent was eliminated in vacuo by adding benzene several times, at a bath temperature not exceeding +5° C.

The compound I was obtained in a yield of 0.9 g of slight ly yellow oil (I). The purification occured by column chromatography on silica gel with a mixture of cyclohexane-ethyl acetate-glacial acetic acid in the ratio 40:60:1. The R$_f$-values, the NMR spectrum and the UV-spectrum were identical with the compound I described in Example 2.

EXAMPLE 3b

In an analogous manner as described in Example 3a, there was prepared the 9-oxo-15S-hydroxy-16,16,20,20-tetramethyl-18-oxa-5cis, 10,13-trans-prostatrienoic acid.

EXAMPLE 3c in an analogous manner as described in Example 3a, there was prepared the 9-oxo-15S-hydroxy-16,16-dimethyl-18-oxa,5cis, 10,13-trans-20-nor-prostatrienoic acid.

EXAMPLE 4

Synthesis of 9,15-dihydroxy-16,16-dimethyl-18-oxa-5cis,10,13-trans-prostatrienoic acid (I)

38 mg of the compound 9-oxo-15-hydroxy-16,16-dimethyl-18-oxa-5cis,10,13-trans-prostatrienoic acid (I) were dissolved in 45 ml of 1,2-dimethoxy ethane. At 0° C., 0.5 ml of a 0.5 molar zinc boron hydride solution (prepared by suspending 2.8 g of zinc chloride in 45 ml of 1,2-dimethoxy ether and adding 1.52 g of sodium boron hydride while cooling and stirring, stirring for half an hour and rapidly filtering of undissolved substances under argon), was added. Stirring was continued at room temperature for 2 and a half hours. Then, the reactant was decomposed with glacial acetic acid at 0° C., the desired product was extracted with ethyl acetate-water. The organic phase was dried with MgSO$_4$ filtered and concentrated in vacuo.

Yield of compound I: 36.5 mg of colorless oil (98%).

The product was purified by column chromatography.

Yield: 26.4 mg of colorless oil.

NMR spectrum (in CDCl$_3$) δvalues:

0.9 singlet 6 H (CH$_3$), 1.19 triplet 3 H (CH$_3$—CH$_2$—), 1.4–2.7 multiplet 12 H (—CH$_2$—,>CH—), 3.3 singlet 2 H (—(CH$_3$)$_2$—C—CH$_2$—O), 3.45 quartet 2 H (—OCH$_2$—CH$_3$), 3.85–4.1 multiplet 2 H(>CH–OH), 5.25–5.75 multiplet 6 H (olefinic H), 6.4–7.0 large signal 3 H (2×OH and 1×COOH).

By exchange of H/D the signal at 6.6–7.2 ppm can be removed.

EXAMPLE 1 d

Synthesis of 9-oxo-11α, 15-dihydroxy-16,16-dimethyl-18-oxa-5-cis-13-trans-20-homo-prostadienoic acid (R$^3$=n-C$_3$H$_7$)

15 S and 15 R epimers (III)

5.9 g of the compound 9-oxo-11α,15-bis-tetrahydropyranyloxy-16,16-dimethyl-18-oxa-5-cis-13-trans-20-homo-prostadienoic acid (II) were dissolved in 15 ml of tetrahydrofurane, 100 ml of acetic acid - water were added in the ratio 2:1 and stirred for 4 hours at 40° C. Then, the solvent was eliminated in vacuo by adding benzene several times, at a temperature not exceeding 5° C.

The yield of compound XII a was 5.1 g of pale oil.

After column chromatography on Merck silica gel (70-230 mesh) with chloroform-methanol (22:1) there were obtained in the fractions (individual fraction: 2ml) 151–282=1.8 g of 15 R epimer III a and the fractions 283–498=1.5 g of 15 S epimer III b.

Yield: 3.3 g (76%).

Thin-layer chromatogram (solvent: ethyl acetate-acetic acid=97.5:2.5) (Merck silica gel plates).

R$_f$=0.37, 15 R epimer
R$_f$=0.29, 15 S epimer

The spectra for the 15 R epimer and 15 S epimer of III a are practically identical within the scope of the customary resolution.

Absorptions in the infrared spectrum (NaCl plates): 3450 (OH band), 2955, 1750 (ketone-carbonyl), 1720 (acid-carbonyl). 1110, 1040, 970.

NMR spectrum (in CDCl$_3$) δ-values:

0.95 singlet 6 H (CH$_3$), 0.95 triplet 3 H (CH$_3$CH$_2$—CH$_2$), 1.2–2.7 multiplet 14 H (—CH$_2$—,>CH—), 3.35 singlet 2 H (—(CH$_3$)$_2$C—CH$_2$O—), 3,4 triplett 2 H (—OCH$_2$CH$_2$CH$_3$), 3.8–4.4 multiplet 2 H (>CH—OH), 5.25–5.75 multiplet 4 H (olefinic H), 5.8–6.5, large singlet 3 H (2×OH, 1×COOH).

By H/D exchange the signal at 5.8–6.5 can be removed.

EXAMPLE 2 d

Synthesis of 9-oxo-15-hydroxy-16,16-dimethyl-18-oxa-5-cis-10,13-trans-20-homo-prostatrienoic acid (R$^3$=n-C$_3$H$_7$)

15 S and 15 R epimer (I)

1.6 g of compound III (Example 1 d) were dissolved in a mixture of 100 ml 66% acetic acid and aqueous 2 N hydrochloric acid, pH 1.5, while thoroughly stirring. The solution was heated to 30–35° C. for two hours, cooled and the reaction mixture was extracted several times with ethyl acetate. The ethyl acetate phase was separated, dried with MgSO$_4$ and concentrated in vacuo.

Yield: 1.3 g of pale oil (I).

Thin-layer chromatogram: (solvent: ethyl acetate - acetic acid =97.5:2.5) (Merck silica gel).

solvent: cyclohexane: ethyl acetate-glacial acid =60:40:1.

R$_f$=0.39, 15 R epimer
R$_f$=0.32, 15 S epimer
R$_f$=0.78

When the isomer mixture of the compound III (Example 1d) is used, the isomer separation of the 15 S or 15 R epimer of compound I occurs by column chromatography on silica gel with a mixture of cyclohexane-ethyl acetate - glacial acetic acid in the ratio 60:40:1.

NMR spectrum (in $CDCl_3$)$\delta$-values: 0.95 singlet 6 H ($CH_3$), 0.95 triplet 3 H (C$H_3$—$CH_2$—$CH_2$), 1.2–2.7 muliplet 12 H (—$CH_2$—>CH—), 3.35 singlet 2 H (—$CH_3$)$_2$>6-C$H_2$—O—), 3.4 triplett 2 H (—OC$H_2$—$CH_2$—$CH_3$), 4.0 multiplet 1 H (>CH—OH), 5.2–5.8 multiplet 4 H (olefinic H), 6.10–6.35 split duplet 1 H (—CH=C$H$—C=O), 6.7–7.3 large signal 2 H (OH and COOH), 7.4–7.65 split dublet 1 H (—C$H$=CH—C=O).

By H/D exchange the signal at 6.7–7.3 ppm can be removed.

The NMR spectra for the 15 S or the 15 R isomer are practically identical within the scope of the customary resolution (60 MHz-spectrum).

UV-spectrum (in ethanol) $c = 9.6 \cdot 10^{-5}$ Mol/ltr:- $\lambda_{max} = 218$ m$\mu$, $\epsilon \approx 10.000$.

EXAMPLE 3 d

Synthesis of
9-oxo-15-hydroxy-16,16-dimethyl-18-oxa-5-cis-10,13-trans-20-homo-prostatrienoic acid ($R^3 = n-C_3H_7$) I 1.0 g of the compound 9-oxo-11α,15-bis-tetrahydropyranyloxy-16,16-dimethyl-18-oxa-5-cis-13-trans-20-homoprostadienoic acid (II) were dissolved in 15 ml of tetrahydrofurane, 25 ml of aqueous hydrochloric acid of pH 1.3 were added and the solution was heated to 35° C. for one and a half hours. Then, the solvent was aliminated in vacuo by adding benzene several times, at a bath temperature not exceeding +5° C.

The compound I was obtained in a yield of 0.9 g of slightly yellow oil (I). The purification occured by column chromatography on silica gel with a mixture of cyclohexane-ethyl acetate-glacial acetic acid in the ratio 60:40:1. The $R_f$-values, the NMR spectrum and the UV-spectrum were identical with the compound I described in Example 2 d.

EXAMPLE 1 e

Synthesis of
9-oxo-11α,15-dihydroxy-16,16-dimethyl-18-oxa-5-cis-13-trans-20-bis-homo-prostadienoic acid ($R^3 = n-C_4H_9$)

15 S and 15 R epimers (III)

5.7 g of the compound 9-oxo-11α,15-bis-tetrahydropyranyloxy-16,16-dimethyl-18-oxa-5-cis-13-trans-20-bis-homo-prostadienoic acid (II) were dissolved in 15 ml of tetrahydrofurane, 100 ml of 66% acetic acid / water were added in the ratio 2:1 and stirred for 4 hours at 40° C. Then, the solvent was aliminated in vacuo by adding benzene several times, at a temperature not exceeding 5° C. The yield of compound XII a was 4.8 g of pale oil.

After column chromatography on Merck silica gel (70–230 mesh) with chloroform-methanol (22:1) there were obtained in the fractions (individual fraction: 2 ml) 101–250 = 1.4 g of 15 R epimer III a and the fractions 255–510 = 1.1 g of 15 S epimer III b.

Yield: 2.5 g (60%).

Thin-layer chromatogram (solvent: ethyl acetate-acetic acid = 97.5:2.5) (Merck silica gel plates).

$R_f = 0.39$, 15 R epimer
$R_f = 0.27$, 15 S epimer

The spectra for the 15 R epimer and 15 S epimer of III a are practically identical within the scope of the customary resolution.

Absorptions in the infrared spectrum (NaCl plates): 3455 (OH band), 2950, 1745 (ketone-carbonyl), 1715 (acid-carbonyl), 1110, 1040, 975.

NMR spectrum (in $CDCl_3$)$\delta$-values: 0.9 singlet 6 H ($CH_3$), 0.9 triplet 3 H (C$H_3CH_2CH_2CH_2$—), 1.1–2.8 multiplet 16 H (—$CH_2$—,>CH—), 3.28 singlet 2 H (—($CH_3$)$_2$>C—C$H_2$—O) 3.46 triplett 2 H (—OC$H_2CH_2CH_2CH_3$), 3.8–4.4 multiplet 2 H (>CH—OH), 5.25–5.75 multiplet 4 H (olefinic H), 5.0–6.1 large singlet 3 H (2 ×OH, 1×COOH).

By H/D exchange the signal at 5.0–6.1 can be removed.

EXAMPLE 2 e

Synthesis of
9-oxo-15-hydroxy-16,16-dimethyl-18-oxa-5-cis-10,13-trans-20-bis-homo-prostatrienoic acid 15 S and 15 R epimer (I) ($R^3 = n-C_4H_9$)

2.0 g of compound III (Example 1) were dissolved in a mixture 100 ml 66% acetic acid and aqueous 2 H hydrochloric acid, pH 1.5, while thoroughly stirring. The solution was heated to 30–35° C. for one and a half hours, cooled and the reaction mixture was extracted several times with ethyl acetate. The ethyl acetate phase was separated, dried with $MgSO_4$ and concentrated in vacuo.

Yield: 1.7 g of pale oil (I).

Thin-layer chromatogram (solvent: ethyl acetate - acetic acid = 97.5:2.5) (Merck silica gel).

$R_f = 0.76$

Solvent : cyclohexan : ethylacetate - glacial add = 60:40:1.

$R_f = 0.38$
$R_f = 0.31$

When the isomer mixture of the compound III (Example 1 e) is used, the isomer separation of the 15 S or 15 R epimer of compound I occurs by column chromatography on silica gel with a mixture of cyclohexane-ethyl acetate - glacial acetic acid in the ratio 60:40:1.

NMR spectrum (in $CDCl_3$)$\delta$-values: 0.9 singlet 6 H ($CH_3$), 0.9 triplet 3 H ($CH_3$—$CH_2$—$CH_2CH_2$—), 1.1–2.8 multiplet 14 H (—$CH_2$—>CH—), 3.3 singlet 2 H (—$CH_3$)$_2$>C—C$H_2$—O—), 3.45 triplett 2 H (—OC$H_2$—$CH_2$—$CH_2$—$CH_3$/ ), 3.95 multiplet 1 H (>CH—OH), 5.2–5.8 multiplet 4 H (olefinic H), 6.05–6.35 split duplet 1 H (—CH=C$H$—C=O), 5.0–5.4 large signal 2 H (OH and COOH) 7.4–7.65 split dublet 1 H (—C$H$=CH—C=O).

By H/D exchange the signal at 5.0–5.4 ppm can be removed. The NMR spectra for the 15 S or the 15 R isomer are practically identical within the scope of the customary resolution (60 MHz-spectrum).

UV-spectrum (in ethanol) $c = 9.6 \cdot 10^{-5}$ Mol/ltr : $\lambda$ max = 218 m$\mu$, $\epsilon \approx 10.000$.

EXAMPLE 3 e:

Synthesis of
9-oxo-15-hydroxy-16,16-dimethyl-18-oxa-5-cis-10,13-trans-20-bis-homo-prostatrienoic acid ($R^3 = n-C_4H_9$)

0.9 g of the compound 9-oxo-11α, 15-bis-tetrahydropyranyloxy-16,16-dimethyl-18-oxa-5-cis-13-trans-20-bis-homo-prostadienoic acid (II) were dissolved in 15 ml of tetrahydrofurane, 25 ml of aqueous hydrochloric acid of pH 1.3 were added and the solution was heated to 35° C. for one and a half hours. Then, the solvent was eliminated in vacuo by adding benzene several times, at a bath temperature not exceeding +5° C.

The compound I was obtained in a yield of 0.7 g of slightly yellow oil (I). The purification occurred by column chromatography on silica gel with a mixture of cyclohexaneethyl acetate-glacial acetic acid in the ratio 60:40:1. The $R_f$-values, the NMR spectrum and the UV-spectrum were identical with the compound I described in Example 2 e.

EXAMPLE 1 f

Synthesis of 9-oxo-11α, 15-dihydroxy-16,16,19-trimethyl-18-oxa-5-cis-13-trans-prostadienoic acid ($R^3$ = i-$C_3H_7$)

15 S and 15 R epimers (III)

1.9 g of the compound 9-oxo-11α, 15-bis-tetrahydropyranyloxy-16,16,18-oxa-5-cis-13-trans-prostadienoic acid (II) were dissolved in 5 ml of tetrahydrofurane, 40 ml of acetic acid / water were added in the ratio 2:1 and stirred for 4 hours at 40° C. Then the solvent was eliminated in vacuo by adding benzene several times, at a temperature not exceeding 5° C.

The yield of compound XII a was 1.7 g of pale oil.

After column chromatography on Merck silica gel (70-230 mesh) with chloroform-methanol (22:1) there were obtained in the fractions (individual fractions: 2 ml) 130-199=0.5 g of 15 R epimer III a and the fractions 230-354=0.3 g of 15 S epimer III b.

Yield: 0.8 g (57% d.Th.).

Thin-layer chromatogram (solvent: ethyl acetate-acetic-acid=97.5:2.5) (Merck silica gel plates).

$R_f$=0.38, 15 R epimer
$R_f$=0.29, 15 S epimer

The spectra for the 15 R epimer and 15 S epimer of III a are practically identical within the scope of the customary resolution.

Absorptions in the infrared spectrum (NaCl plates): 3450 (OH band), 2955, 1750 (ketone-carbonyl), 1720 (acid-carbonyl), 1110, 1043, 970.

EXAMPLE 2 f

Synthesis of 9-oxo-15-hydroxy-16,16,19-trimethyl-18-oxa-5-cis,10,13-trans-prostatrienoic acid ($R^3$ = i-$C_3H_7$)

15 S and 15 R epimer (I)

0.6 g of compound III (Example 1 f) were dissolved in a mixture of 50 ml 66% acetic acid and aqueous 2 H hydrochloric acid, pH 1.5, while thoroughly stirring. The solution was heated to 30°-35° C. for one and a half hours, cooled and the reaction mixture was extracted several times with ethyl acetate. The ethyl acetate phase was separated, dried with MgSO4 and concentrated in vacuo.

Yield: 0.55 g of pale oil (I).

Thin-layer chromatogram (solvent: ethyl acetate / acetic acid=97.5:2.5) (Merck silica gel).

$R_f$=0.76

When the isomer mixture of the compound III (Example 1) is used, the isomer separation of the 15 S or 15 R epimer of compound I occurs by column chromatography on silica gel with a mixture of cyclohexane-ethyl acetate - glacial acetic acid in the ratio 60:40:1.

NMR spectrum (in $CDCl_3$) δ-values:
0.95 singlet 6 H ($CH_3$), 0.92 duplett

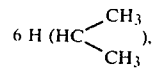

1.2-2.7 multiplet 10 H (—$CH_2$—>CH—), 3.3 singlet 2 H (—$CH_3$)$_2$>C—$CH_2$—O—) 3.4 multiplett

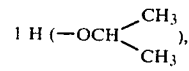

4.1 multiplett 1 H (>CH—OH), 5.25-5.75 multiplet 4 H (olefinic H), 6.05-6.35 split duplet 1 H (—CH=CH—C=O), 5.5-6.2 large signal 2 H (OH and COOH) 7.4-7.65 split dublet 1 H (—CH=CH—C=O).

By H/D exchange the signal at 5.5-6.2 ppm can be removed. The NMR spectra for the 15 S or the 15 R isomer are practically identical within the scope of the customary resolution (60 MHz-spectrum).

UV-spectrum (in ethanol) c=9.6·10$^{-5}$ Mol/ltr : λmax.=218 mμ, ε≈10.000.

EXAMPLE 3 f:

Synthesis of 9-oxo-15-hydroxy-16,16,19-trimethyl-18-oxa-5-cis, 10,13-trans-prostatrienoic acid ($R^3$=i-$C_3H_7$)

1.1 g of the compound 9-oxo-11α, 15-bis-tetrahydropyranyl-16,16,19-trimethyl-18-oxa-5-cis-13-trans-prostadienoic acid (II) were dissolved in 15 ml of tetrahydrofurane, 25 ml of aqueous hydrochloric acid of pH 1.3 were added and the solution was heated to 35° C. for one and a half hours. Then, the solvent was eliminated in vacuo by adding benzene several times at a bath temperature not exceeding +5° C.

The compound I was obtained in a yield of 0.5 g of slightly yellow oil (I). The purification occured by column chromatography on silica gel with a mixture of cyclohexane-ethyl acetate-glacial acetic acid in the ratio 60:40:1. The $R_f$-values, the NMR spectrum and the UV-spectrum were identical with the compound I described in Example 2 f.

What is claimed is:

1. A compound of the formula

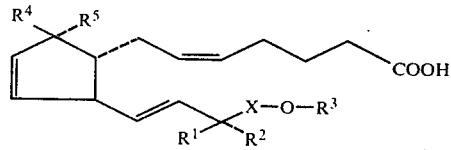

including the optically active compounds of natural configuration and racemic compounds, or a physiologically acceptable salt thereof with an organic or inorganic base, or an ester thereof formed with an aliphatic, cycloaliphatic, or aralphatic alcohol having up to 8 carbon atoms, wherein $R^1$ and $R^2$ are different and are either hydrogen or hydroxy, $R^4$ and $R^5$, taken alone, are different and are either hydrogen or hydroxy, $R^4$ and $R^5$, taken together, are oxygen, $R^3$ is saturated or unsaturated, straight-chain or branched, aliphatic hydrocarbon having 1-8 carbon atoms, and X is

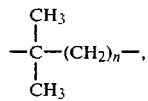

where n is 0,1, or 2.

2. A compound as in claim 1 wherein R³ is straight or branched lower alkyl and X is isopropylidine.

3. A compound as in claim 1 which is 9-oxo-15-hydroxy-16,16-dimethyl-18-oxa-5-cis-10, 13-trans-prostatrienoic acid.

4. A pharmaceutical composition for the treatment of hypertension comprising a therapeutically effective amount, of a compound as in claim 3 together with a pharmaceutically-acceptable carrier therefor.

5. A compound as in claim 1 which is 9-oxo-15-hydroxy-16, 16, 20, 20-tetramethyl-18-oxa-5-cis-10, 13-, transprostatrienoic acid.

6. A pharmaceutical composition for the treatment of hypertension comprising a therapeutically effective amount of a compound as in claim 5 together with a pharmaceutically-acceptable carrier therefor.

7. A compound as in claim 1 which is 9-oxo-15-hydroxy-16, 16-dimethyl-18-oxa-5-cis-10, 13-trans-20-norprostatrienoic acid.

8. A pharmaceutical composition for the treatment of hypertension comprising a therapeutically effective amount of a compound as in claim 7 together with a pharmaceutically-acceptable carrier therefor.

9. A compound as in claim 1 which is 9,15-dihydroxy-16, 16-dimethyl-18-oxa-5-cis-10,13-trans-prostatrienoic acid.

10. A pharmaceutical composition for the treatment of hypertension comprising a therapeutically effective amount of a compound as in claim 9 together with a pharmaceutically-acceptable carrier therefor.

* * * * *